US00PP30900P2

(12) United States Plant Patent
Thorup

(10) Patent No.: US PP30,900 P2
(45) Date of Patent: Sep. 24, 2019

(54) ***VIOLA* PLANT NAMED 'HALO GOLDEN YELLOW'**

(50) Latin Name: *Viola cornuta*
Varietal Denomination: Halo Golden Yellow

(71) Applicant: Ball Horticultural Company, West Chicago, IL (US)

(72) Inventor: Troy Thorup, Chiang Mai (TH)

(73) Assignee: Ball Horticultral Company, West Chicago, IL (US)

( * ) Notice: Subject to any disclaimer, the term of this patent is extended or adjusted under 35 U.S.C. 154(b) by 0 days.

(21) Appl. No.: 15/999,977

(22) Filed: Sep. 6, 2018

(51) Int. Cl.
*A01H 6/00* (2018.01)
*A01H 5/00* (2018.01)

(52) U.S. Cl.
USPC ..... Plt./323

(58) Field of Classification Search
USPC ..... Plt./323
CPC ..... A01H 6/00; A01H 5/00
See application file for complete search history.

*Primary Examiner* — Keith O. Robinson
(74) *Attorney, Agent, or Firm* — Audrey Charles

(57) ABSTRACT

A new and distinct cultivar of *Viola* plant named 'Halo Golden Yellow', characterized by its bright yellow-colored flowers tinted with yellow-orange, medium green-colored foliage, and moderately vigorous, mounded-spreading growth habit, is disclosed.

1 Drawing Sheet

Latin name of genus and species of plant claimed: *Viola cornuta.*

Variety denomination: 'Halo Golden Yellow'.

BACKGROUND OF THE INVENTION

The present invention relates to a new and distinct cultivar of *Viola* plant botanically known as *Viola cornuta* and hereinafter referred to by the cultivar name 'Halo Golden Yellow'.

The new cultivar originated in a controlled breeding program in Guadalupe, Calif. during September 2013. The objective of the breeding program was the development of *Viola* cultivars having large flowers with distinctive flower coloration and a mounded-spreading growth habit.

The new *Viola* cultivar is the result of cross-pollination. The female (seed) parent of the new cultivar is the proprietary *Viola cornuta* breeding selection coded 13-2492-7, not patented, characterized by its dark-yellow-colored flowers, dark green-colored foliage, and vigorous, prostrate growth habit. The male (pollen) parent of the new cultivar is the proprietary *Viola cornuta* breeding selection coded 13-2212-5, not patented, characterized by its medium orange-colored flowers, light green-colored foliage, and moderately vigorous, mounded growth habit. The new cultivar was discovered and selected as a single flowering plant within the progeny of the above stated cross-pollination during March 2014 in a controlled environment in Guadalupe, Calif.

Asexual reproduction of the new cultivar by terminal stem cuttings since March 2014 in Guadalupe, Calif. and Elbum, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Halo Golden Yellow' as a new and distinct cultivar of *Viola* plant:

1. Bright yellow-colored flowers tinted with yellow-orange;
2. Medium green-colored foliage; and
3. Moderately vigorous, mounded-spreading growth habit.

Plants of the new cultivar differ from plants of the female parent primarily in having a different flower color, lighter colored foliage, and a less vigorous, more mounded growth habit. Plants of the new cultivar differ from plants of the male parent primarily in having a different flower color, darker colored foliage, and a more spreading growth habit.

Of the many commercially available *Viola* cultivars, the most similar in comparison to the new cultivar is 'Halo Lemon Frost', U.S. Plant Pat. No. 26,383. However, in side-by-side comparison, plants of the new cultivar differ from plants of 'Halo Lemon Frost' in at least the following characteristics:

1. Plants of the new cultivar have a petal color different from plants of 'Halo Lemon Frost'; and
2. Plants of the new cultivar have a lighter colored spur than plants of 'Halo Lemon Frost'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Halo Golden Yellow'. The plants were approximately three months old. The plants were grown in one-gallon containers for approximately 8 weeks in a greenhouse in Elburn, Ill. Plants were given one pinch one week before transplant.

DETAILED BOTANICAL DESCRIPTION

Figure 1:
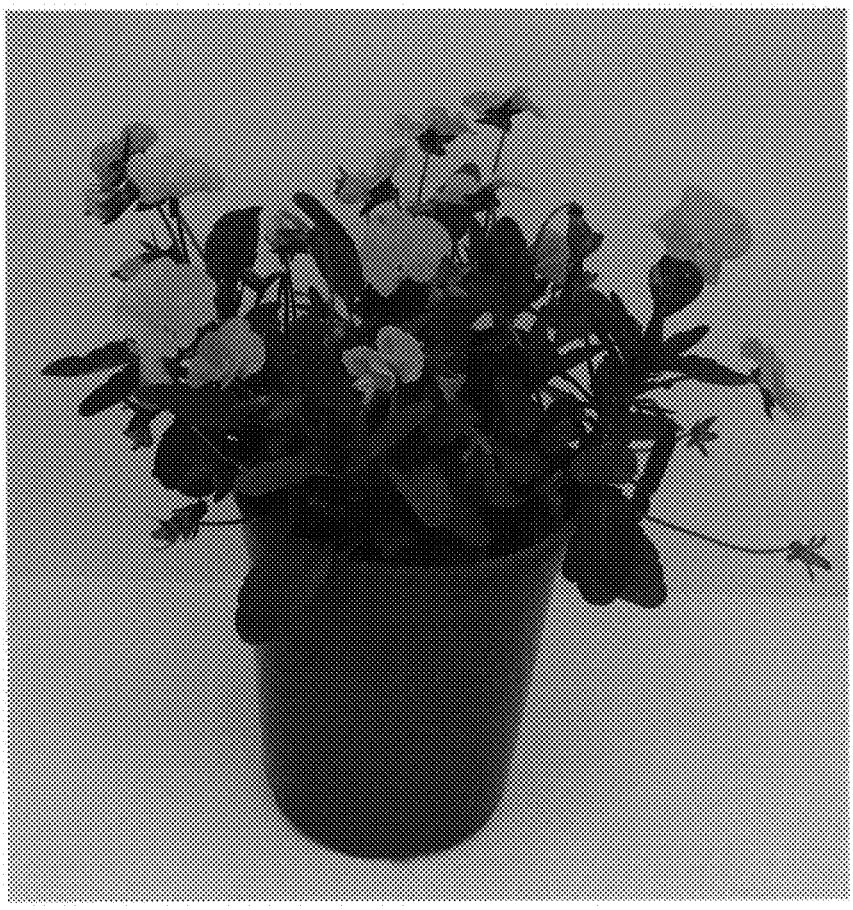
FIG. 1 illustrates a side view of the overall growth and flowering habit of 'Halo Golden Yellow'.
Figure 2:
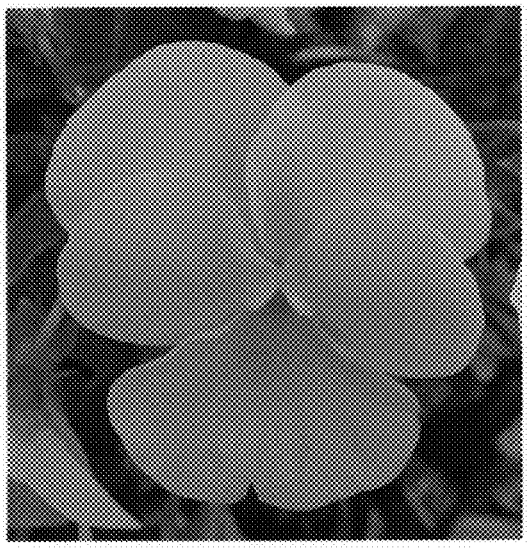
FIG. 2 illustrates a close-up view of an individual flower of 'Halo Golden Yellow'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in July 2018 under natural light conditions in West Chicago, Ill.

The following descriptions and measurements describe approximately three-month old plants produced from cuttings from stock plants and grown under conditions comparable to those used in commercial practice. The plants were grown in one-gallon containers for approximately 8 weeks in a greenhouse in Elburn, Ill. Plants were given one pinch one week before transplant. Greenhouse temperatures in Elburn, Ill. were maintained at approximately 65° F. to 70° F. (18.3° C. to 21.1° C.) during the day and approximately 55° F. to 60° F. (12.8° C. to 15.6° C.) during the night. No supplemental lighting was provided. Measurements and numerical values represent averages of typical plants.

Botanical classification: *Viola cornuta* 'Halo Golden Yellow'.

Parentage:

*Female parent*.—Proprietary *Viola cornuta* breeding selection coded 13-2492-7, not patented.

*Male parent*.—Proprietary *Viola cornuta* breeding selection coded 13-2212-5, not patented.

Propagation:

*Type cutting*.—Terminal stem.

*Time to initiate roots*.—Approximately 7 to 10 days.

*Time to produce a rooted cutting*.—Approximately 35 to 42 days.

*Root description*.—Fine, fibrous.

*Rooting habit*.—Freely branching.

Plant description:

*Commercial crop time*.—Approximately 6 to 8 weeks from a rooted cutting to finish in a 10 cm pot.

*Growth habit and general appearance*.—Herbaceous perennial, moderately vigorous, mounded-spreading.

*Hardiness*.—USDA Zone 5a (−20° F. to −15° F/−28.9 ° C. to −26° C.).

*Size*.—Height from soil level to top of plant plane: Approximately 23.0 cm. Width: Approximately 31.0 cm.

*Branching habit*.—Freely basal branching, pinching enhances basal branching. Quantity of main branches per plant: Approximately 12.

*Lateral branches*.—Strength: Strong, flexible. Length: Approximately 14.5 cm. Diameter: Approximately 4.0 mm. Length of central internode: Approximately 1.0 cm. Texture: Moderately pubescent with very short hairs. Color of young stems: 145B to 145C. Color of mature stems: 145A often tinted with 187A.

Foliage description:

*General description*.—Quantity of leaves per main branch: Approximately 9. Fragrance: None detected. Form: Simple. Arrangement: Alternate.

*Leaves*.—Aspect: Petiole is at an acute angle to stem and leaf blade is perpendicular to downward turning. Shape: Narrowly ovate to narrowly elliptic. Margin: Crenate. Apex: Obtuse. Base: Rounded. Venation pattern: Pinnate. Length of mature leaf at center of stem: Approximately 5.7 cm. Width of mature leaf at center of stem: Approximately 3.0 cm. Texture of upper surfaces: Glabrous. Texture of lower surfaces: Sparsely pubescent on venation. Color of upper surface of young and mature foliage: Closest to 146B with midvein of 146D other venation indistinguishable from lamina. Color of lower surface of young and mature foliage: Closest to 147C with midvein of 146D other venation indistinguishable from lamina.

*Petiole*.—Length: Approximately 2.5 cm. Diameter: Approximately 2.0 mm. Texture: Sparsely pubescent. Color: 146D.

*Stipules*.—Shape: Narrowly Ovate. Margin: Pinnately parted. Apex: Obtuse. Base: Truncate. Length: Approximately 4.0 cm. Width: Approximately 2.0 cm. Texture of upper and lower surfaces: Sparsely pubescent on midveins. Color of upper surface: Closest to 146B. Color of lower surface: Closest to 147C.

Flowering description:

*Flowering habit*.—'Halo Golden Yellow' is freely flowering under outdoor growing conditions with substantially continuous blooming from early spring through autumn.

*Lastingness of individual flower on the plant*.—Approximately 5 to 7 days.

Flower description:

*General description*.—Type: Single, zygomorphic, not persistent. Flower aspect; Upward and outward facing. Quantity per plant: Approximately 22. Fragrance: Slightly sweet.

*Bud*.—Rate of opening: Generally takes 2 to 3 days for bud to progress from first color to fully open flower. Quantity showing color per plant: Approximately 7.

*Bud just before opening*.—Shape: Oblong. Length: Approximately 1.5 cm. Diameter: Approximately 6.0 mm. Color: 146C with petal portion of 12B.

*Corolla*.—Shape: Generally orbicular, with a spur on lower petal. Length: Approximately 4.5 cm. Width: Approximately 4.0 cm. Depth: Approximately 2.0 cm.

*Petals*.—Quantity: Five in a single whorl; two upper petals, two lateral petals and one lower petal with a spur. Shape of upper and lateral petals: Obovate. Shape of lower petal: Obcordate. Appearance: Dull. Margin of all petals: Entire. Apex of upper and lateral petals: Rounded. Apex of lower petal: Obcordate. Base of all petals: Attenuate. Length of upper petals: Approximately 2.2 cm. Width of upper petals: Approximately 2.5 cm. Length of lateral petals: Approximately 2.0 cm. Width of lateral petals: Approximately 2.0 cm. Length of lower petal: Approximately 1.9 cm. Width of lower petal: Approximately 2.6 cm. Texture of upper surface: Glabrous, with base of lateral and lower petals densely glandular pubescent. Texture of lower surface: Glabrous. Color of upper surface of upper petals when first and fully open: 12A. Color of lower surface of upper petals when first and fully open: 12B with base of NN155D. Color of upper surface of lateral petals when first and fully open: 12A tinted with 17A. Color of lower surface of lateral petals when first and fully open: 12B with base of NN155D. Color of upper surface of lower petal when first and fully open: 12A heavily tinted with 17A. Color of lower surface of lower petal when first and fully open: 12B with base of NN155D.

*Spur*.—Quantity: 1 per flower. Length: Approximately 1.0 cm. Diameter at proximal end: Approximately 2.0 mm. Diameter at distal end: Approximately 1.0 mm. Color: NN155D.

*Calyx*.—Shape: Star. Diameter: Approximately 2.5 cm.

*Sepals*.—Quantity per flower: 5 in a single whorl. Shape: Lanceolate. Margin: Entire with erose base. Apex: Acute. Base: Truncate. Length: Approximately 2.2 cm. Width: Approximately 5.0 mm. Texture of upper and lower surfaces: Glabrous. Color of upper and lower surfaces: 146B.

*Peduncle*.—Strength: Moderately strong, flexible. Aspect: Acute angle to stem. Length: Approximately 8.0 cm to 12.0 cm. Diameter: Approximately 2.0 mm. Texture: Glabrous. Color: 146D.

*Reproductive organs*.—Androecium: Stamen quantity: 5 per flower, tightly appressed against ovary. Stamen length: Approximately 4.0 mm, two bear nectar spurs of approximately 6.0 mm in length. Anther shape: Ovoid. Anther length: Approximately 4.0 mm. Anther width: Approximately 2.0 mm. Anther color: 158A with 165B at apex. Pollen amount: Abundant. Pollen color: 4D. Gynoecium: Pistil quantity: 1 per flower. Pistil length: Approximately 7.0 mm. Stigma shape: Globular. Stigma length: Approximately 1.5 mm. Stigma color: 151D. Style length: Approximately 1.5 mm. Style color: 145D. Ovary length: 4.0 mm. Ovary color: 145B.

Seed and fruit production: Neither seed nor fruit production has been observed.

Disease and pest resistance: Resistance to pathogens and pests common to *Viola* has not been observed.

What is claimed is:

1. A new and distinct cultivar of *Viola* plant named 'Halo Golden Yellow', substantially as herein illustrated and described.

* * * * *